US005100911A

United States Patent [19]

Binder et al.

[11] Patent Number: 5,100,911

[45] Date of Patent: Mar. 31, 1992

[54] THIENYLOXYALKYLAMINE DERIVATIVES, PROCESS FOR THEIR PREPARATION AND MEDICAMENTS CONTAINING THEM

[75] Inventors: Dieter Binder, Vienna; Gerhard Greier, Linz; Franz Rovenszky, Bruck an der Leitha; Friedrich Hillebrand, Unterach, all of Austria

[73] Assignee: Ebewe Arzneimittel Gesellschaft m.b.H., Unterach, Austria

[21] Appl. No.: 490,566

[22] PCT Filed: Sep. 12, 1989

[86] PCT No.: PCT/AT89/00084

§ 371 Date: May 15, 1990

§ 102(e) Date: May 15, 1990

[87] PCT Pub. No.: WO90/02743

PCT Pub. Date: Mar. 22, 1990

[30] Foreign Application Priority Data

Sep. 15, 1988 [AT] Austria ............................... 2266/88

[51] Int. Cl.[5] .................... A61K 31/40; C07D 295/04; C07D 333/32; C07D 409/14

[52] U.S. Cl. .................................... 514/422; 514/212; 514/320; 514/444; 540/596; 546/196; 548/574; 549/64

[58] Field of Search .......................... 549/64; 548/574; 546/196; 540/596; 514/212, 320, 422, 444

[56] References Cited

U.S. PATENT DOCUMENTS 4,778,803 10/1988 Binder ................................. 549/64
4,814,330 3/1987 Binder ............................. 514/231.5

FOREIGN PATENT DOCUMENTS 0266336 3/1987 European Pat. Off. .
2600065 6/1986 France .

OTHER PUBLICATIONS

Binder et al., "Thiophene as a Structural . . . ", CA 102:220824m, 1985.

*Primary Examiner*—C. Warren Ivy
*Assistant Examiner*—Celia Chang
*Attorney, Agent, or Firm*—Spencer & Frank

[57] ABSTRACT

Thienyloxyalkylamine derivatives of the general formula:

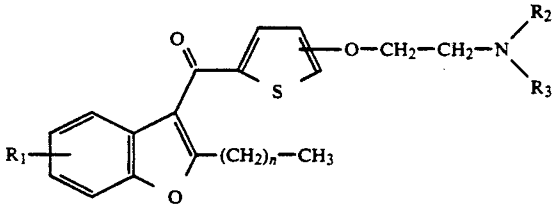

I wherein $—O—CH_2—CH_2—NR_2R_3$ is in position 4 or 5 of the thiophene ring;

$R_1$ is hydrogen, halogen, $CF_3$, alkyl or alkoxy;

$R_2$ and $R_3$ are the same or different and are each alkyl, cycloalkyl, alkenyl or alkynyl each having up to 8 C atoms, or $NR_2R_3$ is a 5 to 7-membered saturated heterocyclic ring optionally containing a further hetero atom which is oxygen or nitrogen optionally substituted by an alkyl group having 1 to 3 C atoms; and n is an integer of 1 to 5; as well as their acid addition salts, are suitable for treatment of heart rhythm disturbances.

10 Claims, No Drawings

THIENYLOXYALKYLAMINE DERIVATIVES, PROCESS FOR THEIR PREPARATION AND MEDICAMENTS CONTAINING THEM

The invention relates to new therapeutically-valuable thienyloxyalkylamine derivatives of the general formula

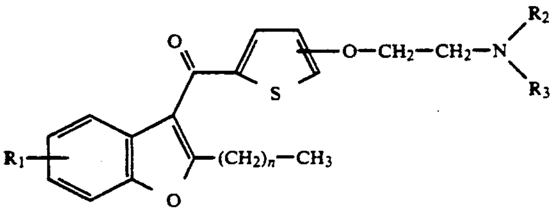

I wherein $-O-CH_2-CH_2-NR_2R_3$ is in position 4 or 5 of the thiophene ring;

$R_1$ is hydrogen, halogen, $CF_3$, alkyl or alkoxy;

$R_2$ and $R_3$ are the same or different and are each alkyl, cycloalkyl, alkenyl or alkynyl each having up to 8 C atoms, or $NR_2R_3$ is a 5 to 7-membered saturated heterocyclic ring optionally containing a further hetero atom which is oxygen or nitrogen optionally substituted by an alkyl group having 1 to 3 C atoms; and n is an integer of 1 to 5;

and their pharmaceutically-acceptable acid addition salts.

The new thienyloxyalkylamine derivatives exhibit advantageous anti-arrhythmic activity and have particular application in circulatory problems.

A preferred class of compounds of general formula I is that in which $R_1=H$ and $n=3$.

The invention also relates to a process for the preparation of the new compounds of general formula I, in which a compound of the general formula

II

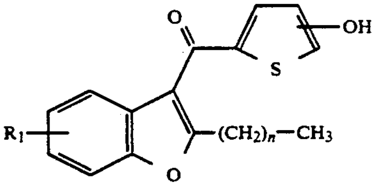

wherein OH is in the 4 or 5-position of the thiophene ring and $R_1$ and n are as defined above, is reacted with a compound of the general formula $$X-CH_2-CH_2NR_2R_3 \quad III$$

wherein $R_2$ and $R_3$ are as defined above and X is Cl, Br, or I, in the presence of at least one equivalent of a strong base, in an inert organic solvent, and, optionally, converting the resultant base of formula I into the acid addition salt.

The reaction according to the invention is best conducted in a manner such that a compound of formula II is dissolved in an inert organic solvent such as, e.g. dimethylformamide (DMF), dimethyl sulphoxide (DMSO) or diethyl carbonate, and reacted with at least one equivalent of a strong base, preferably an alkali metal alkoxide or hydride, and, when an alkali metal alkoxide is used, the alcohol which is obtained or used as solvent for the alkoxide is distilled off. The reaction temperature for this is between 60° and 120° C. Reaction with the compound of the general formula III follows at a temperature between 50° and 100° C. The reaction time is then between 30 minutes and 2 hours.

Because the free bases of the general formula I are generally only poorly crystallisable and are generally undecomposed distillable oils, it is desirable to carry out purification via easily-crystallisable acid addition compounds, such as e.g. the hydrochloride, which can be easily recrystallised.

For this purpose, the crude base is dissolved in a suitable solvent, e.g. in a lower alcohol or ether, at least an equivalent amount of protic acid is added, the solvent is removed under vacuum and the residue is crystallised from methanol, ethanol or, preferably, acetone, optionally with the addition of ether.

These acid addition salts can be obtained in conventional manner, e.g. using alkalis or ion-exchangers, converted into the free compounds, from which they can be obtained by reaction with inorganic or organic acids, in particular those which are suitable for the formation of therapeutically-usable salts.

On account of the close relations between the new compounds and their salts, the corresponding salts are to be understood within the free bases, above and below, as the sense and object make necessary.

The compounds of general formula II can be prepared from compounds of formula IV already known in the literature, in which the $-OCH_3$ group is in position 4 (S. Gronowitz, Ark. Kemi, 12, 239 (1958)) or 5 (J. Sice, J. Am. Chem. Soc. 75, 3697 (1953)) of the thiophene ring, and the compounds of formula VI known from the literature (e.g. N. P. Buu-Hoi, N. D. Xuong and N. V. Bac, J. Chem. Soc. (1964) 173), in which $R_1$ and n are as defined above, according to the following reaction scheme, according to conventional chemical working methods familiar to the skilled man:

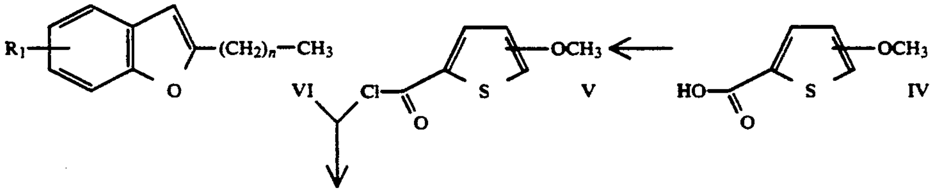

VI V IV

-continued

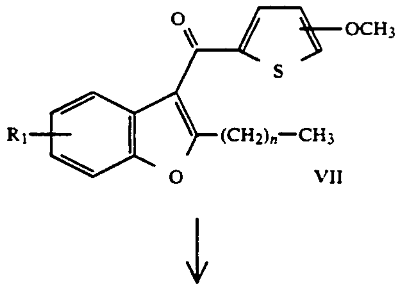

VII

II

The compounds of formula III can be prepared starting from the compounds VIII known from the literature, insofar as they are not already known in the literature or commercially-available, in a manner known to the skilled man, e.g.

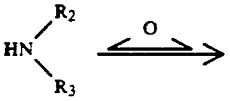

VIII

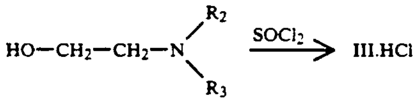

IX

The acid addition salts of the end compounds can be converted into the free bases in a manner known per se, for example by the addition of an alkali or by using ion-exchangers. Other salts can be obtained therefrom by reaction with inorganic or organic acids, in particular those that are suitable for the formation of therapeutically-usable and pharmaceutically-acceptable salts.

Suitable examples of such pharmaceutically-acceptable salts are, in addition to the salt of hydrochloric acid, those of hydrobromic acid, sulphuric acid, nitric acid, phosphoric acid, sulphonic acid, acetic acid, benzoic acid, maleic acid, tartaric acid, citric acid and the like. However, other salts can also be used.

The new compounds of formula I and their pharmaceutically-acceptable salts exhibit outstanding anti-arrhythmic properties.

On account of these pharmacological properties, the new compounds can be used alone or in admixture with other active compounds, in the form of conventional galenic preparations as medicaments for illnesses having heart rhythm perturbations as symptoms, such as, e.g. tachycardia.

Among the types of tachycardia which can be treated with the compounds according to the invention, supraventricular tachycardia, ventricular tachycardia, ventricular ectopia and "reentry" tachycardia, are examples.

The invention also relates to medicaments which find use, e.g. in the form of pharmaceutical preparations, which contain the compounds of general formula I of the invention in admixture with pharmaceutical, organic or inorganic, carrier materials suitable for enteral or parental applications, for example water, gelatin, gum arabic, lactose, starch, magnesium stearate, talc, vegetable oils, polyalkylene glycols, vaseline or the like.

The pharmaceutical preparations can be prepared in solid form, e.g. as tablets, coated tablets, dragees, suppositories, capsules, microcapsules, or in fluid form, e.g. as solutions, solutions for injection, suspensions or emulsions, or in compositions for delayed release of the active ingredient.

If desired, they are sterilised and/or contain additives such as preservatives, stabilisers or emulsifiers, salts for altering osmotic pressure, or buffers.

In particular, pharmaceutical preparations can contain the compounds according to the invention in combination with other therapeutically-valuable substances. The compounds according to the invention can be formulated with the substances together with the additives and/or carrier materials given above, into combination preparations.

The new compounds may be present in the pharmaceutical compositions according to the invention in an amount of about 20 to 200 mg/tablet, the remainder being a pharmaceutically-acceptable excipient.

A suitable dosage for the administration of the new compounds is about 2 to 20 mg/kg per day, but other dosages may be appropriate according to the condition of the patients to be treated. The new compounds can be administered in a plurality of doses and by the oral route.

The new compound [3-(2-butylbenzo[b]furanyl)][5-(2-diethylaminoethoxy-2-thienyl)]methanone hydrochloride, as a representative compound of the new class of substances, has been tested for its anti-arrhythmic properties both in vivo and in vitro. In the Langendorf isolated perfused heart, the substance exhibited a clear anti-arrhythmic effect with a marked sodium-antagonistic constituent. The substance is active at a considerably lower concentration than the comparative anti-arrhythmic Amiodarone.

By contrast to the anti-arrhythmics comprising Class 1, the compound has the advantage that it achieves a simultaneous increase of the conduction times and the refractory times of the heart, and there is also no arrhythmogenic potency. In the reperfusion arrhythmia narcotised dog model, the compound is active in a dosage of 2 mg per kg bodyweight in respect of ventricular arrhythmias, and converts them into a sine-wave. By contrast to conventional anti-arrhythmics of Class 1C, there is no effect on the haemodynamic. The following Examples illustrate the invention without limiting it.

EXAMPLE 1

[3-(2-Butylbenzo[b]furanyl)][5-(2-diethylaminoethoxy)-2-thienyl]methanone Hydrochloride To a solution of 7.1 g (23.7 mmol) (2-butyl-3-benzo[b-]furanyl) (5-hydroxy-2-thienyl)methanone in 140 ml diethyl carbonate, 29.5 ml of a 1 molar methanolic sodium methoxide solution were added and then reacted in an oil bath heated to 123° C. MeOH was distilled off until the reaction mixture reached a temperature of 110° to 112° C. It was then cooled and, at a temperature of 35° to 40° C., a solution of 4.1 g (30.2 mmol) 2-diethylaminoethyl chloride (prepared by separation of 5.8 g of 2-diethylaminoethyl chloride hydrochloride (FLUKA Type No. 31810) between 100 ml saturated sodium bicarbonate solution and 40 ml ether, triple extraction of the aqueous phase each with 30 ml ether, drying and evaporation of the combined organic phases) in 57 ml diethyl carbonate was added. Heating to 90° to 93° C. followed after the end of the addition. A fine yellow precipitate came out of the suspension. After 50 minutes, evaporation followed, the oily crystalline residue was distributed between 350 ml of a saturated sodium bicarbonate solution and 200 ml ether, and stirred, and the phases were separated. The $H_2O$ phase was agitated three times with ether, and the combined organic phases were dried over sodium sulphate/active carbon and evaporated. 9.0 g of an orange oil (95% of theory) were obtained.

The crude product was dissolved in 120 ml absolute ether and dry HCl gas was introduced with cooling. The slightly viscous hydrochloride obtained was crystallised and the bright yellow crystals were filtered with suction. The ca. 10 g raw product thus obtained were dissolved in 180 ml absolute acetone, filtered, and the solution was concentrated to 100 ml. It was cooled, and the crystallisation was completed overnight in the freezer.

The resultant crystals were suction-filtered and washed with cold acetone.

Yield: 7.5 g colourless crystals (73% theory).

M.p.: 130°-132° C.

| Microelemental analysis: $C_{22}H_{29}NO_3S$ (436.02) | C | H | N |
|---|---|---|---|
| calculated: | 63.36 | 6.94 | 3.21 |
| found: | 63.22 | 6.93 | 3.15 |

$^1$H-NMR: ($CDCl_3$):

δ(ppm): 13-11 (very broad; 1H; HCl); 7.61-7.19 (m; 5H; 4 Bz—H and Th—$H_3$); 6.37 (d; 1H; Th—$H_4$); 4.79 (t; 2H; —$OCH_2$); 3.52 (t; 2H; —$NCH_2$); 3.28(q; 4H; —$N(CH_2—CH_3)_2$); 2.96 (t; 2H; Ar—$CH_2$); 1.90-1.25 (m; 4H; —$CH_2$—$CH_2$—); 1.46 (t; 6H. —$N(CH_2CH_3)_2$; 0.91 (t; 3H; —$CH_3$).

The starting material can be prepared as follows:

5-Methoxy-2-thiophenecarbonyl chloride 15.0 g (94.8 mmol) 5-methoxy-2-thiophenecarboxylic acid were heated in 100 ml thionyl chloride and 1 ml abs. DMF for 30 minutes under reflux. The excess thionyl chloride was then distilled off under vacuum. The crude product (ca. 18 g brownish oil) was quickly distilled.

Yield: 14.6 g yellowish oil (87% theory).

Boiling point: 70°-75° C./0.04 mbar.

(2-Butyl-3-benzo[b]furanyl) (5-methoxy-2-thienyl)methanone 3.0 g (17.2 mmol) 2-butylbenzo[b]furan were dissolved in 30 ml abs. chloroform, the solution was cooled to 0° C., and reacted with 3.6 g (20.4 mmol) 5-methoxy-2-thiophenecarbonyl chloride, dissolved in 5 ml abs. chloroform, and then, at a temperature between 0° and 3° C., 2.8 ml $SnCl_4$ were added dropwise. Stirring for 2 hours at 0° C. followed. The reaction mixture was evacuated under ice-cooling over 50 ml 2N HCl, the phases were separated and the aqueous phase thoroughly extracted with ether. The chloroform and ether phases were each washed with 50 ml 2N NaOH, combined, dried over sodium sulphate and evaporated. The crude product was quickly distilled.

Yield: 4.4 g bright yellow oil (81% theory).

Boiling point: 145°-148° C./0.03 mbar.

(2-Butyl-3-benzo[b]furanyl) (5-hydroxy-2-thienyl)methanone 10.0 g (31.8 mmol) 2-butyl-3-benzo[b]furanyl) (5-hydroxy-2-thienyl)methanone in 100 ml abs. chloroform was cooled to 15° C., and reacted with 10 ml (106 mmol) boron tribromide at a temperature between 15° and 20° C. The reaction mixture was then heated under reflux.

Evacuation over 300 ml 2N HCl followed after 1.5 hours, and vigorous stirring for 10 minutes; the phases were separated and the aqueous phase was extracted twice with methylene chloride. The combined organic phases were agitated 5 times each with 120 ml saturated sodium bicarbonate solution. The combined aqueous phases were acidified with conc. HCl and extracted with methylene chloride. The combined organic phases were dried over sodium sulphate/active carbon, filtered and evaporated. The crude product was used directly in the next step.

Yield: 7.6 g viscous oil (80% theory).

| Microelemental analysis: $C_{17}H_{16}O_3S$ (300.21) | C | H |
|---|---|---|
| calculated: | 67.98 | 5.37 |
| found: | 68.04 | 5.42 |

$^1$H-NMR: (In $CDCl_3$ the compound exists in 3 tautomeric forms a, b and c)

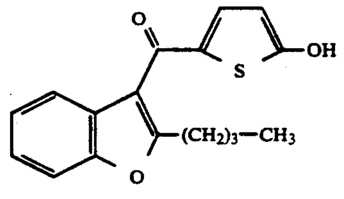

a

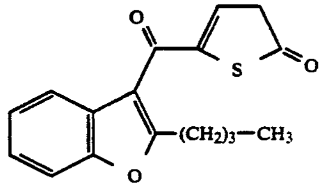

b

-continued

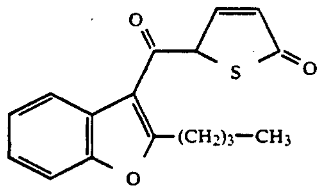

c a: δ(ppm): 7.60–7.15 (m; 4H; Bz—H); 7.42 (d; 1H; Th—$H_3$); 6.18 (d; 1H; Th—$H_4$); 2.85 (t; 2H; Ar—$CH_2$); 1.98-1.10 (m; 4H; —$CH_2$—$CH_2$); 0.90 (t; 3H; —$CH_3$).

b: δ(ppm): 7.60–7.15 (m; 4H; Bz—H); 6.66 (d; 1H; Th—$H_3$); 3.76 (d; 2H; Th—$H_4$); 2.85 (t; 2H; Ar—$CH_2$); 1.98-1.10 (m; 4H; —$CH_2$—$CH_2$); 0.90 (t; 3H; —$CH_3$).

c: δ(ppm): 7.70 (dd; 1H; Th—$H_4$); 7.60–7.15 (m: 4H; Bz—H); 6.45 (d; 1H; Th—$H_3$); 5.88 (dd; 1H; Th—$H_2$); 2.85 (t; 2H; Ar—$CH_2$); 1.98–1.10 (m; 4H; —$CH_2$—$CH_2$); 0.90 (t; 3H; —$CH_3$).

EXAMPLE 2

[3-(2-Butylbenzo[b]furanyl][5-(2-(1-pyrrolidinyl)ethoxy-2-thienyl]methanone Hydrochloride 6.00 g (20.0 mmol) [3-(2-butylbenzo[b]furanyl)](5-hydroxy-2-thienyl)methanone were dissolved in 120 ml diethyl carbonate and reacted with 4.60 ml 5.6M sodium methoxide solution. Introduction into a hot oil bath, at 135° C., followed, and the distillation off of methanol under a nitrogen stream, until the boiling point of the reaction mixture was 115° C. Cooling followed and, at a temperature of 35° to 40° C., a solution of 3.50 g (26.3 mmol) 1-(2-chloroethyl)pyrrolidine (released from 4.50 g of the hydrochloride, FLUKA Type No. 23065) in 60 ml diethyl carbonate was added dropwise. After completion of the addition, heating to 90°–95° C. followed. After 1 hour, evaporation followed, the viscous crystalline residue was distributed between 30 ml saturated sodium bicarbonate solution and 200 ml ether, and stirred, and the phases were separated. The aqueous phase was then agitated three times with a total of 300 ml ether, and the combined organic phases were dried over sodium sulphate and evaporated. 6.73 g of a brown oil were obtained.

This product was suspended in 50 ml 4N hydrochloric acid and heated under reflux for 10 minutes. It was then neutralised with 4N sodium hydroxide and extracted five times with a total of 500 ml ether. The combined organic phases were dried over sodium sulphate, filtered and evaporated.

The crude product was taken up in 100 ml abs. ether and dry hydrogen chloride was introduced with cooling. The resultant crystalline product was vacuum-filtered and crystallised from ethyl acetate.

Yield: 7.00 g colourless crystals (80.7% theory).

M.p.: 137°–139° C. (ethyl acetate).

| Microelemental analysis: $C_{23}H_{28}NClO_3S$ (434.00) | C | H | N |
|---|---|---|---|
| calculated: | 63.65 | 6.50 | 3.23 |
| found: | 63.42 | 6.54 | 3.17 |

$^1$H-NMR: ($CDCl_3$)

δ(ppm): 7.56–7.19 (m; 5H; Bz—H and Th—$H_3$); 6.37 (d; 1H; Th—$H_4$); 4.75 (t, 2H, —O—$CH_2$—); 3.80–3.50 (m, 6H, —$CH_2$—N(—$CH_2$)$_2$); 2.96 (t; 2H; Ar—$CH_2$—); 2.10 (m; 4H; Pyr: —$CH_2$—$CH_2$); 1.90-1.30 (m, 4H, —$CH_2$—$CH_2$—$CH_3$); 0.91 (t; 3H; —$CH_3$).

EXAMPLE 3

[3-(2-Butylbenzo[b]furanyl)][4-(2-diethylaminoethoxy)-2-thienyl]methanone Hydrochloride 3.50 g (11.7 mmol) [3-(2-butylbenzo[b]furanyl)](4-hydroxy-2-thienyl)methanone were dissolved in 70 ml diethyl carbonate and reacted with 2.70 ml of a 30% sodium methoxide solution. Introduction into a hot oil bath at 135° C. followed, and distillation off of methanol in a nitrogen stream, until, after 3 hours, the boiling point of the reaction mixture was 120° C. Cooling followed and, at a temperature of 35° to 40° C., a solution of 1.74 g (12.8 mmol) 2-diethylaminoethyl chloride (released from 2.20 g hydrochloride, FLUKA Type No. 31810) in 20 ml diethyl carbonate was added dropwise. On completion of the addition, heating to 90° to 95° C., and stirring overnight, followed. The solvent was distilled off, the residue distributed between 100 ml saturated sodium bicarbonate solution and 100 ml ether, and stirred, and the phases were separated. The aqueous phase was extracted three times with a total of 200 ml ether and the combined organic phases were dried over sodium sulphate and evaporated.

The residue (3.20 g brown oil) was purified by column chromatography (100 g silica gel, eluent:ethyl acetate). 1.95 g of a yellow oil were obtained.

This was taken up in 50 ml abs. ether and hydrogen chloride was introduced to saturation. The viscous hydrochloride thus obtained was brought to crystallation by grinding and the bright yellow crystals were vacuum-filtered. The crude product thus obtained was recrystallised from 20 ml ethyl acetate.

Yield: 1.52 g bright yellow, hygroscopic crystals (29.9% theory).

M.p.: 70°–71° C. (ethyl acetate).

| Microelemental analysis: $C_{23}H_{30}NClO_3S.1.1\ H_2O$ (455.83) | C | H | N |
|---|---|---|---|
| calculated: | 60.60 | 7.12 | 3.07 |
| found: | 60.45 | 6.80 | 3.14 |

$^1$H-NMR: ($CDCl_3$)

δ(ppm): 7.47–6.92 (m; 5H; Bz—H and Th—$H_3$); 6.96 (d; 1H; Th—$H_5$); 4.95 (t, 2H, —O—$CH_2$—); 3.52–3.00 (m, 6H, —$CH_2$—N(—$CH_2$)$_2$); 3.00–2.52 (m; 5H; Ar—$CH_2$—+HCl+$H_2$O); 1.94–1.42 (m, 4H, —$CH_2$—$CH_2$); 1.42 (t; 6H; —N—$CH_2$—$CH_3$); 0.91 (t, 3H, —$CH_3$).

The starting material can be prepared as follows:

4-Methoxy-2-thiophenecarbonyl chloride 24.0 g (152 mmol) 4-methoxy-2-thiophenecarboxylic acid were suspended in 250 ml thionyl chloride and heated for two hours under reflux. The excess thionyl chloride was then distilled off under vacuum. The crude product was quickly distilled off and crystallised out in the receiver.

Yield: 20.0 g bright yellow crystals (74.6% theory).

M.p.: 40° C.

Boiling point: 122°–124° C./15 mbar.

[3-(2-Butylbenzo[b]furanyl)](4-methoxy-2-thienyl)methanone 15 g (87.1 mmol) 2-butylbenzo[b]furan were dissolved in 75 ml abs. chloroform and reacted at room temperature with 18.6 g (0.11 mol) 4-methoxy-2-thiophenecarbonyl chloride in 20 ml abs. chloroform. At room temperature, 31.8 g (0.12 mol) tin (IV) chloride were added dropwise within 10 min. After stirring for two hours at 25° C., the reaction mixture was poured into a mixture of 150 ml ice, 15.0 ml conc. hydrochloric acid and 50.0 ml water.

The aqueous phase was extracted three times with a total of 300 ml methylene chloride. The combined organic phases were washed with 100 ml saturated sodium bicarbonate solution, dried and evaporated. 29.4 g of a brown oil were obtained which was purified by column chromatography (400 g silica gel, eluent:petroleum ether:benzene = 3:1). The combined pure fractions were quickly distilled.

Yield: 9.12 g gold-yellow, viscous oil (33.3% theory).

Boiling point: 140°-150° C./0.007 mbar.

| Microelemental analysis: $C_{18}H_{18}O_3S$ (314.41) | C | H |
|---|---|---|
| calculated: | 68.76 | 5.77 |
| found: | 68.81 | 5.74 |

$^1$H-NMR: ($CDCl_3$):

δ(ppm): 7.53-7.18 (m; 5H; Bz—H and Th—$H_3$); 6.77 (d; 1H; Th—$H_5$); 3.80 (s, 3H, —$OCH_3$); 2.79 (t, 2H, Ar—$CH_2$—); 1.97-1.15 (m, 4H, —$CH_2$—$CH_2$)$_2$—); 0.90 (t, 3H, —$CH_3$).

[3-(2-Butylbenzo[b]furanyl)](4-hydroxy-2-thienyl)methanone 8.54 g (27.0 mmol) [3-(2-butylbenzo[b]furanyl)](4-methoxy-2-thienyl)methanone were dissolved in 100 ml abs. chloroform and cooled to −10° C. At a temperature between −10° and −5° C., 22.5 g boron tribromide were added over 10 minutes, and the reaction mixture was then stirred for 30 minutes at 0° C.

Pouring onto a mixture of 100 ml methylene chloride, 50 g ice and 25 ml conc. hydrochloric acid, stirring, separation of the phases and extraction of the aqueous phase three times with a total of 200 ml methylene chloride followed. The combined organic phases were washed once with 50 ml 2N hydrochloric acid, dried over sodium sulphate, stirred with active carbon, filtered and evaporated.

Yield: 6.32 g black, viscous oil (77.9% theory).

-continued

| Microelemental analysis: $C_{17}H_{16}O_3S$ (300.38) | C | H |
|---|---|---|
| calculated: | 67.98 | 5.37 |
| found: | 67.73 | 5.41 |

$^1$H-NMR: ($CDCl_3$):

δ(ppm): 7.61-7.15 (m; 5H; Bz—H and Th—$H_3$); 7.50-7.30 (s broad, 1H, —OH); 6.77 (d; 1H; Th—$H_5$); 2.93 (t, 2H, Ar—$CH_2$—); 1.95-1.11 (m, 4H, —$CH_2$—$CH_2$); 0.88 (t, 3H, —$CH_3$).

We claim:

1. Thienyloxyalkylamine compounds of formula:

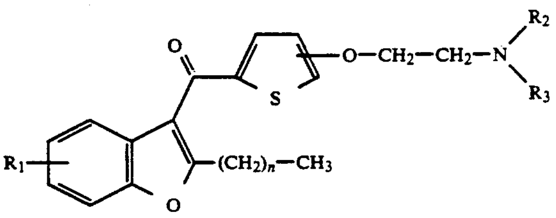

I wherein —O—$Ch_2$—$CH_2$—$NR_2R_3$ is in position 4 or 5 of the thiophene ring;

$R_1$ is hydrogen, halogen, $CF_3$, alkyl or alkoxy;

$R_2$ and $R_3$ are the same or different and are each alkyl cycloalkyl, alkenyl or alkynyl each having up to 8 C atoms, or $NR_2R_3$ is a 5 to 7-membered saturated heterocyclic ring; and n is an integer of 1 to 5;

and their pharmaceutically-acceptable acid addition salts.

2. Compounds of general formula I as defined in claim 1, wherein $R_1$ is hydrogen and n = 3.

3. A compound as defined in claim 2, said compound being [3-(2-Butylbenzo[b]furanyl)][5-(2-diethylaminoethoxy)-2-thienyl]methanone.

4. A compound as defined in claim 2, said compound being [3-(2-Butylbenzo[b]furanyl)][5-(2-(1-pyrrolidinyl-)ethoxy)-2-thienyl]methanone.

5. A compound as defined in claim 2, said compound being [3-(2-Butylbenzo[b]furanyl)][4-(2-diethylaminoethoxy)-2-thienyl]methanone.

6. A compound as defined in claim 2, said compound being [3-(2-Butylbenzo[b]furanyl)][5-(2-diethylaminoethoxy)-2-thienyl]methanone hydrochloride.

7. A compound as defined in claim 2, said compound being [3-(2-Butylbenzo[b]furanyl)][5-(2-(1-pyrrolidinyl-)ethoxy)-2-thienyl]methanone hydrochloride.

8. A compound as defined in claim 2, said compound being [3-(2-Butylbenzo[b]furanyl)][4-(2-diethylaminoethoxy)-2-thienyl]methanone hydrochloride.

9. A pharmaceutical composition for treating arrhythmia, comprising an anti-arrhythmic effective amount of a compound according to claim 1 and a pharmaceutically-acceptable carrier.

10. A method of treating arrhythmia comprising administering an anti-arrhythmic effective amount of a compound according to claim 1.

* * * * *